United States Patent [19]

Watson

[11] Patent Number: 4,708,475

[45] Date of Patent: Nov. 24, 1987

[54] PORTABLE LUMINESCENCE SENSOR

[75] Inventor: Robert D. Watson, Brigham City, Utah

[73] Assignee: Atlantic Richfield Company, Los Angeles, Calif.

[21] Appl. No.: 739,713

[22] Filed: May 31, 1985

Related U.S. Application Data

[63] Continuation of Ser. No. 706,739, Feb. 28, 1985, abandoned, which is a continuation-in-part of Ser. No. 509,681, Jun. 30, 1983, abandoned.

[51] Int. Cl.[4] ............................................. G01N 21/64
[52] U.S. Cl. ................................ 356/417; 250/458.1; 356/419
[58] Field of Search ............... 250/253, 339, 349, 353, 250/372, 458.1, 459.1, 461.1; 356/317, 416, 417, 419, 221, 222, 224, 225

[56] References Cited

U.S. PATENT DOCUMENTS

| | | | |
|---|---|---|---|
| 3,598,994 | 8/1971 | Markle | 250/458.1 |
| 3,641,344 | 2/1972 | Markle | 250/458.1 |
| 3,769,516 | 10/1973 | Markle et al. | 356/317 |
| 3,864,037 | 2/1975 | Johnson | 250/213 VT |
| 4,045,670 | 8/1977 | Anderson et al. | 250/353 |
| 4,195,932 | 4/1980 | Popelka | 356/419 |
| 4,236,071 | 11/1980 | Chimenti | 250/461.1 |
| 4,433,245 | 2/1984 | Poultney | 250/458.1 |
| 4,478,513 | 10/1984 | Skinner et al. | 356/323 |

OTHER PUBLICATIONS

Slater, *Remote Sensing Optics and Optical Systems*, 1980, pp. 269-287.

*Primary Examiner*—F. L. Evans
*Attorney, Agent, or Firm*—James H. Phillips; Michael E. Martin

[57] ABSTRACT

Apparatus is provided to sense and measure solarinduced luminescence, as well as reflectance, within the field of view of a target window for receiving a composite ray of light from the target. A first filter within the path of the composite ray of light transmits a first narrowband component thereof, including a predetermined Fraunhofer Line frequency, to a first sensor. A second narrowband component thereof, proximate the Fraunhofer Line frequency, is directed to a second sensor such that ratios of the electromagnetic energy impinging, respectively, on the first and second sensors may be determined. A removable filter tray assembly carrying the narrowband filters and fine tuning means are employed to facilitate the selection of the predetermined Fraunhofer Line frequency.

15 Claims, 11 Drawing Figures

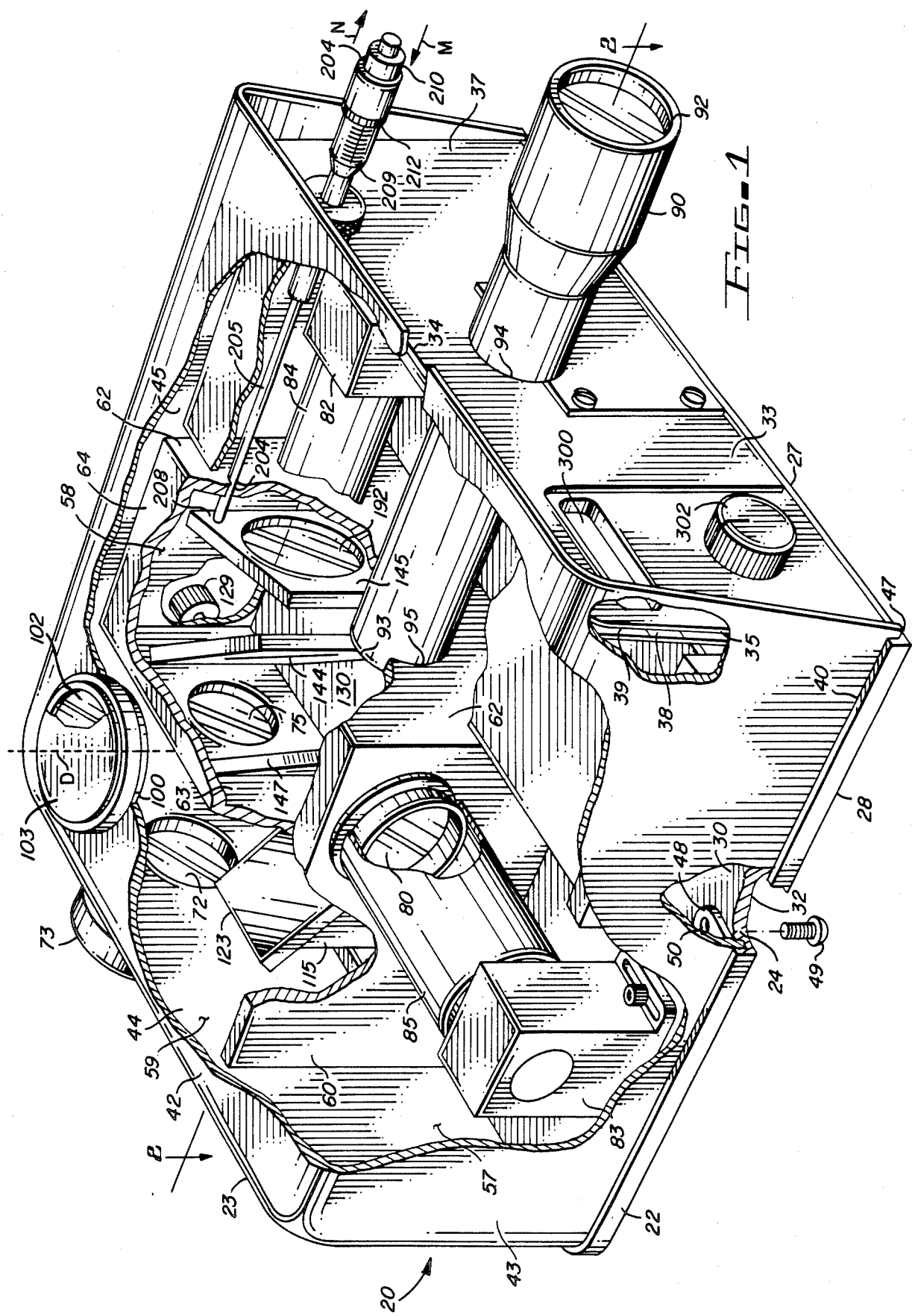

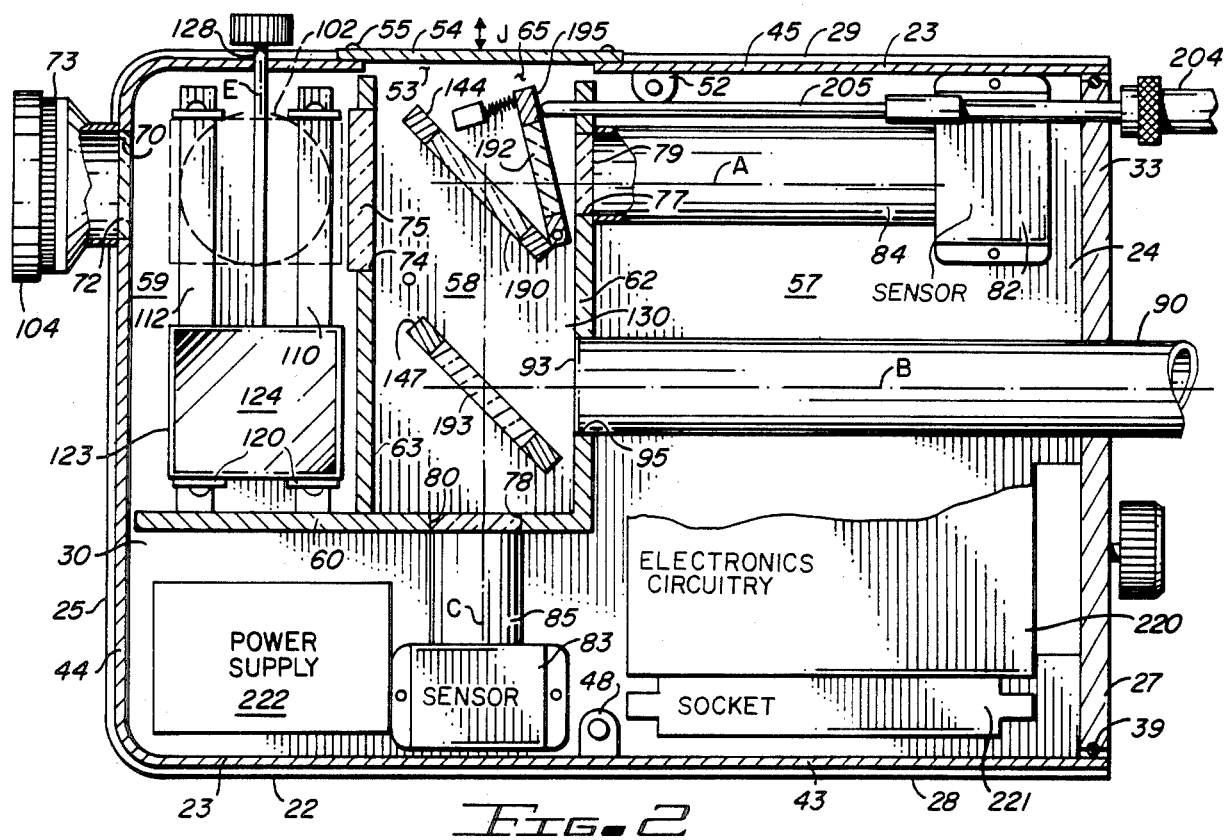
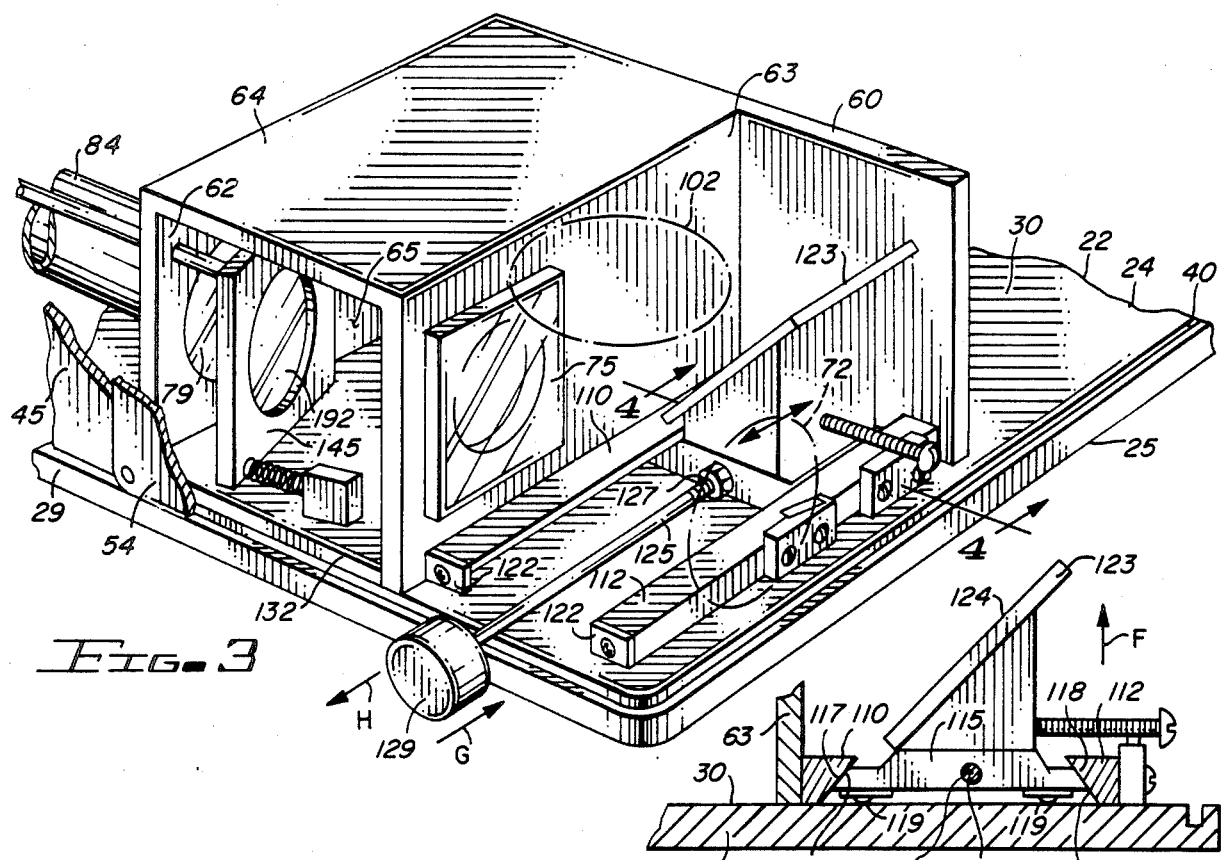

PORTABLE LUMINESCENCE SENSOR

CROSSREFERENCE TO RELATED APPLICATION

This application is a continuation of: U.S. patent application Ser. No. 706,739; entitled "Portable Luminescence Sensor" filed Feb. 28, 1985; by Robert D. Watson; and assigned to the same assignee as this application; which is a continuation-in-part of U.S. patent application Ser. No. 509,681; filed June 30, 1983; entitled "Portable Luminescence Sensor"; by Robert D. Watson; assigned to the same assignee as this application through mesne assignments; and both now abandoned.

FIELD OF THE INVENTION

This invention relates to the radiometer arts and, more particularly, to a handheld radiometer which employs Fraunhofer Line sensing technology to detect and measure the luminescence of materials in the presence of direct sunlight.

BACKGROUND OF THE INVENTION

The known prior art apparatus for sensing luminescence of targets stimulated by direct sunlight and employing Fraunhofer Line sensing technology has been limited to elaborate, bulky, and heavy systems typically built for use in an aircraft or proposed for use in a satellite.

More particularly, the known prior arts constituted the Fraunhofer Line Discriminator (FLD) instrument used for some years by the U.S. Geological Survey (USGS) at Flagstaff, Ariz. and at other locations. This instrument is described in U.S. Pat. No. 3,769,516. Additional U.S. Pat. Nos. 3,578,848; 3,598,994; 3,641,344; and 4,433,245 cover various aspects of the USGS instrument and other contemplated large scale instruments employing Fraunhofer Line sensing technology.

The portable luminescence sensor disclosed herein differs markedly from the airborne/satellite-borne Fraunhofer Line sensing instruments in that it is lightweight and compact and therefore suitable for portable use on the ground by an individual or small team during field exploration and investigative activities.

It is well known in the physical sciences art that the spectrum of sunlight, as it impinges upon the earth, is not uniform but contains many dark lines of narrow bandwidth. The dark lines constituting the absorption spectrum exhibited by sunlight are frequently called Fraunhofer Lines. There are numerous such lines of which Fraunhofer, early in the nineteenth century, first observed the most prominent. To these particular lines he assigned letters for reference purposes. These most prominent lines, together with their designation, origin, and aproximate wavelengths, are listed as follows:

| A | Terrestrial Oxygen | 7594 A | Extreme Red |
| B | Terrestrial Oxygen | 6867 A | Red |
| C | Solar Hydrogen | 6563 A | Red |
| D1 | Solar Sodium | 5896 A | Yellow |
| D2 | Solar Sodium | 5890 A | Yellow |
| E | Solar Iron | 5270 A | Green |
| F | Solar Hydrogen | 4861 A | Blue |
| G | Solar Iron and Calcium | 4308 A | Violet |
| H | Solar Calcium | 3968 A | Extreme Violet |

The lines of solar origin (all those listed except A and B) are due to absorption by gases and vapors in the solar atmosphere. Similarly, the lines of terrestrial origin (A and B) are due to absorption by gases and vapors in the terrestrial atmosphere. The presence of Fraunhofer Lines in the spectrum is used to sense and measure the luminescence emanating from targets illuminated by direct sunlight.

The fundamental technique utilized to detect and measure luminescence takes advantage of the fact that sunlight, whether direct or reflected, is "coded" by a sharp reduction in spectral energy at certain wavelengths; i.e., at the Fraunhofer lines which are absorption features in the solar spectrum. Luminescence, on the other hand, is not so coded; it has a broad and rather uniform spectral output at least over moderate spectral bandwidths. Thus, a purely reflective scene having no luminescence component will replicate the ratio obtained in pure sunlight of the energy in a narrow band within a selected Fraunhofer Line to the energy in an equal bandwidth in the neighboring continuum; i.e., reflected sunlight is coded. A scene containing luminescence, however, changes the code by disturbing the ratio. As will be explained in more detail below, the energy from the sun in a unit bandwidth proximate the Fraunhofer Line is conventionally designated as quantity "a", while quantity "b" is the corresponding level within the Fraunhofer absorption band. For the earth scene, quantities "d" and "c" represent the corresponding continuum and in-band levels as modified by the scene content if it contains a luminescing component. The quantities a, b, c, and d, all measurable (at least as to their relative intensities), permit the development of equations from which luminescence "L" and refelectance "R" coefficients may be determined. It may be noted that the term "luminescence" as used herein comprehends both fluorescence (which is characterized by rapid decay after the exciting energy source is removed) and phosphorescence (which decays more slowly). In the case of solar stimulated reemission, it is not necessary to be concerned with rapid-time responses nor with distinguishing between fluorescence and phosphorescence.

In their fundamental form, the reflectance (R) and luminescence (L) equations are:

$$R = [(d-c)/(a-b)]$$

$$L = [(d/a) - R]$$

Because of the need to measure very precisely the energy within a very narrow Fraunhofer Line to obtain two of the four quantities required to determine luminescence and reflectance, the airborne/satellite-borne systems have universally contemplated the use of extremely narrow filters which, of necessity, are large, heavy, expensive, and must be temperature controlled. Instruments of this type use Fabry-Perot glass spacer etalons. The performance of these filters is well known in the art; however, their aforementioned physical characteristics render them undesirable for use in a Fraunhofer Line sensing instrument intended for handheld use on the ground under field exploration and investigation conditions.

It has been generally thought that a relatively inexpensive, handheld, stable, field-usable instrument employing Fraunhofer Line sensing technology to detect and measure luminescence was not achievable. However, by invention disclosed herein, measurements are taken of the energy within a Fraunhofer Line without resorting to the use of Fabry-Perot etalons or other extremely narrow-band equivalents.

OBJECTS OF THE INVENTION

It is therefore a broad object of this invention to provide an improved portable luminescence detection instrument which employs Fraunhofer Line sensing technology.

Accordingly, it is an object of the present invention to provide improved means and method for sensing and measuring luminescence emanating for a selected target.

Another object of the invention is the provision of luminescence sensor of substantially reduced weight and bulk rendering the sensor hand portable.

And another object of the invention is to provide a portable luminescence sensor which is relatively insensitive to temperature variations within a range as may occur during a typical day of field use and in which such temperature variations as occur may be compensated for by a simple and accurate adjustment.

Yet another object of the invention is the provision of a portable luminescence sensor having a readily changeable optical assembly to accommodate a selected luminescent target.

Still another object of the invention is to provide a portable luminescent sensor which functions independently of a concurrent reading of direct sunlight.

Yet still another object of the invention is the provision of a portable luminescence sensor having conveniently operable tuning means to adjust for optimum signal input.

Still a further object of the invention is the provision of a portable luminescence sensor which is comparatively simple and is inexpensive to fabricate.

Yet a further object of this invention is to provide a portable luminescence sensor which is relatively unencumbered and substantially maintenance free.

And a further object of the invention is the provision of a device of the foregoing character which may be assembled in a manually portable package.

SUMMARY OF THE INVENTION

Briefly, to achieve the desired objects of the instant invention, in accordance with a preferred embodiment thereof, there is first provided an instrument housing having a target window for admitting a composite beam of light emanating from a target and traveling along a first optical path. A first filter disposed within the housing and aligned along the first optical path: (a) transmits a first component of the composite beam of light, which first beam component comprises a selected waveband including an intermediate selected Fraunhofer Line, and (b) redirects the balance of the composite beam of light as a second beam component traveling along a second optical path.

A second filter, also aligned along the first optical path, further narrows the bandpass or the first beam component as received from the first filter to a waveband of predetermined width in the frequency range which includes, but is broader than, the selected Fraunhofer Line. A third filter aligned along the second optical path narrows the second beam component to a predetermined waveband in the continuum offset from the Fraunhofer Line by a selected frequency difference. Each filter is angularly adjustable relative the respective optical path. Tuning means for effecting calibrated vernier angular adjustment are further associated with the second filter.

The first beam component is received by a first sensor which provides an indication of the energy level of the impinging light. Similarly, the second beam component is received by a second sensor which provides an indication of the energy level of the light impinging thereon. Means are provided to convert the sensor outputs to sensible indicia.

In accordance with further aspects of the preferred embodiment, a viewing scope is provided for observing the target through the target window. The first, second and third filters are carried by a tray which is interchangeably receivable within the housing. Additionally, serially oriented highpass and lowpass optical filters may also be provided to block the entrance into the instrument of light components falling outside the visible light range.

Further provided are means for receiving sunlight into the instrument and directing the sunlight along a third optical path. A reflective diverter is selectively positionable to divert light from the third optical path to alternatively travel along the first optical path and encounter the first filter.

DESCRIPTION OF THE DRAWING

The subject matter of the invention is particularly pointed out and distinctly claimed in the concluding portion of the specification. The invention, however, both as to organization and method of operation, may best be understood by reference to the following detailed description taken with reference to the subjoined claims and the accompanying drawing of which:

FIG. 1 is a perspective view, partially broken away for purposes of illustration, of a portable luminescence sensing and measuring instrument embodying the principles of the instant invention;

FIG. 2 is a horizontal sectional view taken along the line 2—2 of FIG. 1;

FIG. 3 is an enlarged fragmentary perspective view of the lens and filtering portion of the device seen in FIG. 2;

FIG. 4 is a fragmentary vertical sectional view taken along the line 4—4 of FIG. 3;

DETAILED DESCRIPTION OF THE INVENTION

Figure 5:
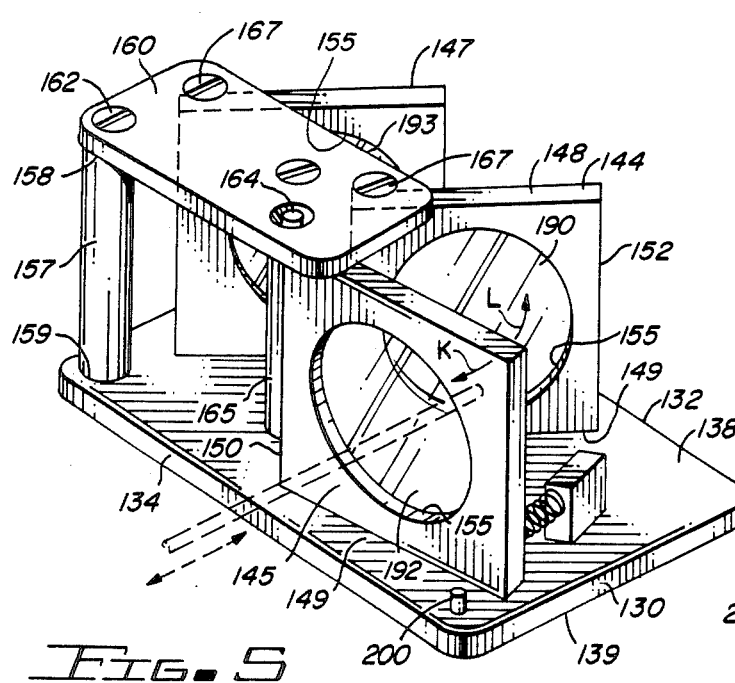
FIG. 5 is an enlarged perspective view of an interchangeable filter tray assembly usable in the instrument.

A portable luminescence sensor, embodying the principles of the instant invention, will now be described with reference to the drawing. First, the structure of a representative embodiment will be described in detail. Subsequently, the operation and function will be delineated. In the ensuing narrative, like reference characters will denote correspnding elements throughout the several views.

Structure

Attention is first directed to FIG. 1 which illustrates a preferred embodiment of a portable luminescence sensor constructed in accordance with the teachings of the instant invention. The body of the device is in the form of a case or housing, generally designated by the reference character 20, having a base structure 22 and a removable cover structure 23. With further reference to FIG. 2, it is seen that the primary support member of base structure 22 is generally rectangular base plate 24 having forward edge 25, rearward edge 27, left edge 28, right edge 29, and top and bottom surfaces 30 and 32, respectively. (The terms: "forward", "rearward", "left", and "right" are used herein for purposes of orientation in the ensuing description. Similarly, edges 28 and 29 are considered to be longitudinal while edges 25 and 27 are considered to be lateral. Such terms are set forth for purposes of convenience and not limitation.)

Rear panel 33, having upper edge 34, upward left edge 35 and upright right edge 37, projects upwardly from rear edge 27 of base plate 24. Seal groove 38, carrying seal 39, extends continuously along edges 34, 35, and 37. Cover receiving groove 40, formed in top surface 30 of base plate 24, extends continuously at a location spaced slightly inboard from edges 25, 28, and 29.

Cover structure 23, being somewhat in the form of an inverted box, includes generally rectangular top panel 42, having integral, depending, continuous left, forward, and right side panels 43, 44, and 45, respectively. The several side panels terminate with continuous lower edge 47 which, in the assembled configuration, is received in groove 40. In order to provide a light impervious union between base structure 22 and cover structure 23, the continuous under surface of top panel 42 and side panels 43 and 45 are received in sealing engagement against seal 39.

A tab 48, projecting inwardly from side panel 43, is positioned to rest upon top surface 30 of base plate 24 when edge 47 is fully received within groove 40. Screw 49, received through a clearance sized opening (not illustrated) in base plate 24, threadedly engages aperture 50 in tab 48 for detachable securement of cover structure 23 to base structure 22 in accordance with conventional technique. A similar tab 52 for a like purpose is seen projecting inwardly from side 45 in FIG. 2. As will be apparent to those skilled in the art, additional attachment structures may be periodically spaced throughout the arrangement. Similarly, while screw 49 has been specifically illustrated as a machine screw, it will be appreciated that other commercially available fastening elements may be readily substituted.

An opening 53, the purpose of which will be discussed presently, is formed through right side panel 45. Cover plate 54, removably secured to the exterior of right side panel 45, as by sheet metal screws 55, normally closes opening 53. To insure a light impervious assembly, a flat gasket-type seal may reside between cover plate 54 and right side panel 55.

The interior of case 20 is partitioned into first, second and third compartments 57, 58, and 59, respectively, by an arrangement of panels extending upwardly from the top surface 30 of base plate 24. First panel 60, intermediate and parallel to left and right edges, 28 and 29, respectively, extends longitudinally from proximate forward edge 25 to an intermediate terminal location. Second panel 62 is transverse, extending between first panel 60 and right edge 29. Third panel 63 is also transverse, extending between first panel 60 and right edge 29, at an intermediate location between second panel 62 and forward edge 25. Cover panel 64, having respective edges adjoining the panels 60, 62 and 63, overlays compartment 58. Accordingly, compartment 58 has an open end 65 in substantial alignment with opening 53 through right side panel 45 of cover structure 23.

The housing 20 may be fabricated of various materials by respectively suitable manufacturing techniques. For example, case 20 may be structured of metal, such as aluminum, by appropriate stamping techniques. Similarly, the housing may be molded of a plastic material. The several components may be integrally formed or, alternately, individually shaped and assembled by employing fastening devices or adhesives compatible with the selected material. Such devices are well known in the art as are commercially available cases which may be modified for the immediate purpose.

In accordance with the immediately preferred embodiment of the instant invention, the several optical elements are lined along prescribed interrelated axes. For purposes of illustration and reference during the ensuing description, these axes are designated as first, second, third, and fourth, as represented by the broken lines indicated by the alphabetic reference characters A, B, C, and D, respectively. As shown in FIG. 2, axes represented by the reference characters A, B, and C, lie in a single plane with the former two extending in longitudinal parallelism. The latter is laterally extending, being a perpendicular bisector of the former. The axis represented by the reference character D, being perpendicular to the described plane, intersects the axis represented by the reference character A. Each of the designated axes is considered the longitudinal axis of an optical path along which a ray of light moves.

An opening 70 is formed through forward side panel 44 of cover structure 23. An ultra-violet cutoff optical filter 72, of a standard commercially available type as will be known to those skilled in the art, is fixed in opening 70 by any suitable lens mounting means, such as a suitable adhesive. Tubular shield 73 projects forwardly from panel 44. For inclusive reference, opening 70, filter 72, and shield 73, having axis A as the common center, is termed the target window.

Opening 74, extending through third panel 63, carries infra-red cutoff optical filter 75. Filter 75, secured within opening 74 by conventional means in alignment with axis A, is likewise of standard commercial manufacture.

Aperture 77 is formed through second panel 62. Aperture 78 is similarly formed through first panel 60. Objective lenses 79 and 80 are mounted within apertures 77 and 78, respectively. Lens 79 is aligned along axis A. Lens 80 is aligned along axis C. Each of the lens 79, 80 is of the familiar configuration generally referred to as focusing lens. Hereinafter, lens 79 will be referred to as first objective lens while lens 80 will be referred to as second objective lens.

First sensor 82, residing in compartment 57, is aligned along axis A. A second sensor 83, also residing within compartment 57, is aligned along axis C. Representative of the sensor 82 and 83, is the blue enhanced photovoltaic silicon device manufactured by Silicon Detector Corporation, under the Identification No. sd-200-12-12-241. As supplied by the manufacturer, the device is provided with outwardly directed flanges at the base for attachment to base plate 24 by conventional screws. Tubular element 84 provides light tight communication between lens 79 and sensor 82. Similarly, tubular element 85 provides a light impervious path between lens 80 and sensor 83.

Viewing scope 90, having ocular end 92 and objective end 93, extends through openings 94 and 95 in rear panel 33 and second panel 62, respectively. Field end 93 terminates in the approximate plane of panel 62. Ocular end 92 is spaced rearwardly of panel 33. Viewing scope 90 may be of any commercially available type conventionally used as a sight for rifles or other firearms. Although a relatively low magnification in the range of 1× to 3× power is preferred, scopes of greater power or variable power are contemplated.

A conventional annular lens holder 100 is secured within an appropriate opening through top panel 42 of cover structure 23. Diffusing plate 102 is carried by lens holder 100. Lens holder 100 projects upwardly from top panel 42 and removably receives lens cover 103 in accordance with standard practice. As a preferred standard, diffusing plate 102 is free from fluorescence with a twenty percent light transmission as will be readily understood by those in the lens making art. Plate 102, the relative position of which is shown in broken outline in FIGS. 2 and 3, is aligned along axis D. The relative positioning of optical filter 72 is also seen in broken outline in FIG. 3. A second lens cover 104, generally similar to lens cover 103, is detachably securable to tubular shield 73.

Diverter means for selectively and optionally receiving light entering case 20 through lens 102 along the optical path represented by the broken line D and redirecting the light along the optical path represented by the broken line A in a direction toward sensor 82 resides within compartment 59. As more clearly viewed in FIGS. 3 and 4, the immediately preferred diverter means includes a pair of spaced apart parallel ways 110 and 112. The ways reside along a transverse axis, represented by the broken line E which, when observed in plan view, is perpendicular to the axis represented by the broken line A. Being generally triangular in cross-section, and secured to the top surface 30 of base plate 24 by any convenient expedience, ways 110 and 112 carry elongate guide surfaces 113 and 114, respectively. Guide surfaces 113 and 114 are in opposition and appear in cross-section as being mutually, downwardly, outwardly divergent.

Slide 115 is disposed between ways 110 and 112. Carried by slide 115 are opposed outwardly, downwardly, divergent contact surfaces 117 and 118 which are matingly received against the guide surfaces 113 and 114, respectively. Spring loaded plungers 119, of conventional commercially available configurations, carried by slide 115, bear against surface 30 of base plate 24, urging slide 115 upwardly in the direction of arrowed line F, maintaining surfaces 117 and 118 in juxtaposition with and bearing against the respective guide surfaces 113 and 114. The travel of slide 115 in either direction along axis E is limited by positive stops. In the immediately preferred embodiment, the stops assume the form of interference tabs 120 carried at the inner end of ways 110 and 112 and interference tabs 122 affixed to the outer end. For expedience, a commercial dove-tail slide (e.g., Velmer model A-1503A) may be adapted for the foregoing purpose.

Mirror 123, having reflective surface 124, is supported at an oblique angle by slide 115. Operating rod 125 projects from slide 115 parallel to axis E. The fixed end 127, of operating rod 125, is threadedly engaged within slide 115. Free end 128 of operating rod 125 resides external of case 120. Hand knob 129 is carried at free end 128.

Mirror 123, in response to manual manipulation of hand knob 129, is selectively movable in alternate directions along axis E between a first position and a second position. The first position is obtained by applying manual pressure to hand knob 129 in the direction of arrowed line G, correspondingly moving slide 115 against inner stops 120. Movement of hand knob 129 in the direction indicated by arrowed line H, relocates mirror 123 in the second position wherein slide 115 bears against outer stops 122. With mirror 123 in the first position, light entering through filter 72 is free to travel along the axis represented by the arrowed line A, as previously described. With mirror 123 in the second position, the normal optical path of light entering through lens 102 along the axis represented by the broken line D (see FIG. 1) is redirected along the axis represented by the broken line A in a direction toward sensor 82. For optimum operation, it is apparent that the physical center of reflecting surface 124, when in the second position, should reside at the intersection of axes A and D. Further, reflective surface 124 should be oriented at forty-five degrees to each of the associated optical paths.

Equivalent structural configurations for achieving the desired function will readily occur to those skilled in the art. For example, slide 115 may be movable upon spring loaded gibs of traditional design. Various detent means may be substituted for the interference tabs and allow for the removal of slide 115. Similarly, the movement of slide 115 may be in response to a manually rotated or motor driven lead screw.

Figure 6:
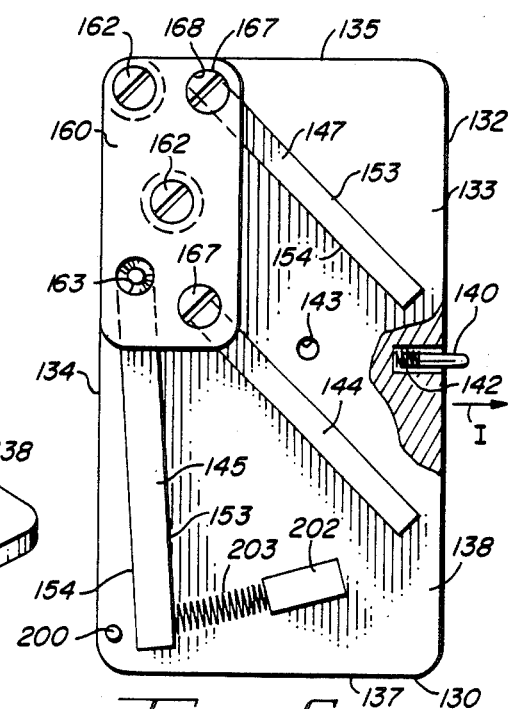
FIG. 6 is a top plan view of the filter tray assembly seen in FIG. 5, a portion thereof being broken away to reveal additional detail.

A filter tray assembly 130, detailedly depicted in the enlarged enhancements of FIGS. 5 and 6, removably resides within compartment 58. Filter tray assembly 130 includes base 132 which, described in reference to the assembled relationship with case 20, includes forward edge 133, rearward edge 134, inner edge 135, outer edge 137, and top and bottom surfaces 138 and 139, respectively. Plunger 140, normally biased in the direction of arrowed line I by compression spring 142 and being of known configuration, projects from forward edge 133. Threaded aperture 143 extends through base 132 between surfaces 138 and 139.

Filter tray assembly 130, along with the associated structure to be subsequently described, is removable and replaceable through opening 53 is right side panel 45 of cover structure 23. The lower portion of the surface of second panel 62 adjacent compartment 58 functions as an alignment surface for receiving rearward edge 134 which serves as a complemental alignment surface thereagainst. Similarly, the surface of third panel 63 adjacent compartment 58 functions as a contact surface for receiving the contact end of plunger 140, thereagainst. Plunger 140 and spring 142 function as biasing means for urging the alignment surfaces into juxtaposition. Accordingly, base 132 is slidable within compartment 58 in selective opposite directions as indicated by the double arrowed line J. In the inward direction, surface 135 abuts first panel 60 to provide stop means. A bolt, receivable through an opening in base plate 24 and threadedly engagable within aperture 143, brings surface 139 of base 132 into contact with top surface 30 of base plate 24 to positionally retain filter tray assembly 130. The opening through base plate 24 and the bolt, although not specifically herein illustrated, are conventional for the intended purpose as will be appreciated by those skilled in the art.

Supported by base 132 are first, second, and third filter holders 144, 145, and 147, respectively. For convenience of manufacture, each filter holder is identical, being generally rectangular and including parallel upper and lower edges 148 and 149, respectively, and parallel upright edges 150 and 152. Also included are opposing faces 153 and 154. An aperture 155 extends through each filter holder between faces 153 and 154.

Each filter holder is pivotally supported in a generally upright position for rotational, angular adjustment. A stand-off post, having upper end 158 and lower end 159, rises substantially perpendicularly from top surface 138 of base 132, proximate the apex of edges 134 and 135. Although not specifically herein illustrated, lower end 159 is secured to base 132 by any conventional known means, such as a bolt extending through base 132 and threadedly engaged within post 157. Support plate 160, cantileveredly extending over at least a portion of each of the filter holders, is secured to the upper end 158 of post 157, as by flat head machine screw 162.

Filter holder 145 is affixed to tray 132 by pivot means including bore 163 extending through support plate 160 and an aligned bore (not illustrated) extending through base 132. Pin 164, carried proximate upright end 150, subtends edges 148 and 149 and is rotatably journaled within respective bores. In the assembled configuration, as seen in FIG. 2, the axis of rotation of pin 164 is perpendicular to the plane defined by the axes A, B, and C. To prevent binding and insure free rotation of filter holder 154, an auxiliary stand-off post 165 extends between base 132 and plate 160 at a location spaced from stand-off post 157.

A portion of each of the filter holders 144 and 147, adjacent the respective upright edge 150, resides between base 132 and support plate 160. Extending into each filter holder 144 and 147, from the respective top edge 148 and the respective upright edge 150, is a threaded aperture (not specifically illustrated), which receives a respective flat head machine screw 167 extending through an appropriate sized countersunk bore 168 in plate 160.

Figure 7:
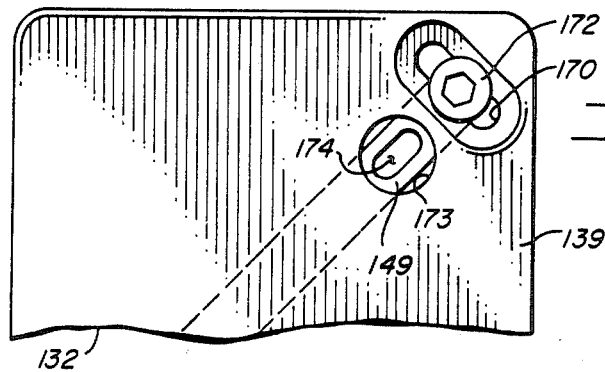
FIG. 7 is an enlarged bottom plan view of a fragmentary portion of the filter tray assembly of FIG. 5, especially illustrating a preferred means for adjusting the [lens] filter holders.

Filter holders 144 and 147 are secured to base 132 as clearly seen with reference to FIG. 7. An opening 170 is formed through base 132 in alignment with countersunk bore 168. Preferably, opening 170 is elongated in a direction perpendicular to the normal residence direction of lower edge 149 of the respective filter holder. A bolt 172, herein illustrated as a socket head cap screw, extends through opening 170 and is threadedly received within an opening in the respective filter holder aligned with the threaded opening receiving the screw 167. Accordingly, each filter holder 144 and 147 is rotatable about an axis parallel to the axis of pin 164.

As further seen in FIG. 7, a bore 173 extends through base 132 along an axis substantially parallel to the axis of rotation, and spaced from opening 170 in a direction along the normal residence position of the respective filter holder. A slot 174, elongated in a direction parallel to the faces 153 and 154, is formed into the lower edge 149 of each filter holder 144 and 147.

Figure 8:
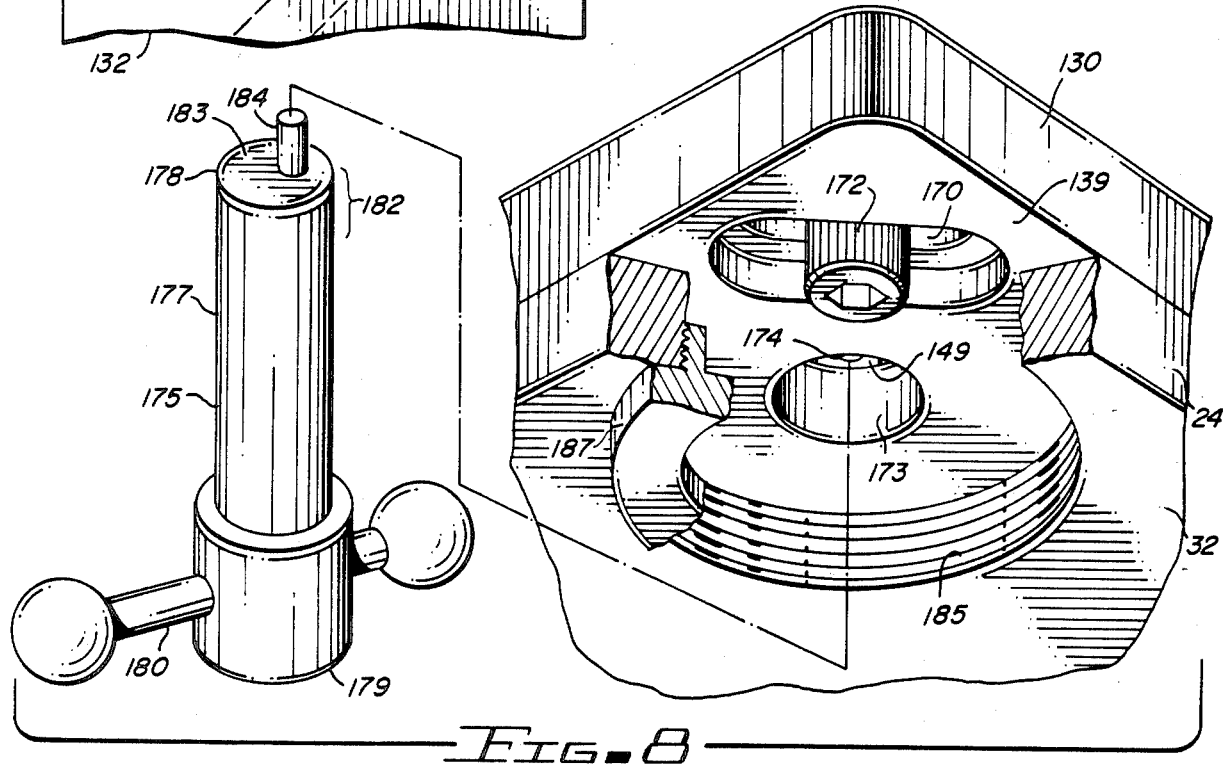
FIG. 8 is further enlarged perspective view of the portion of the filter tray assembly seen in FIG. 7, as it would appear when assembled with the instrument of FIG. 1 (the instrument being shown in fragmentary perspective) and further illustrating an adjusting tool for use in combination therewith.
Figure 9:
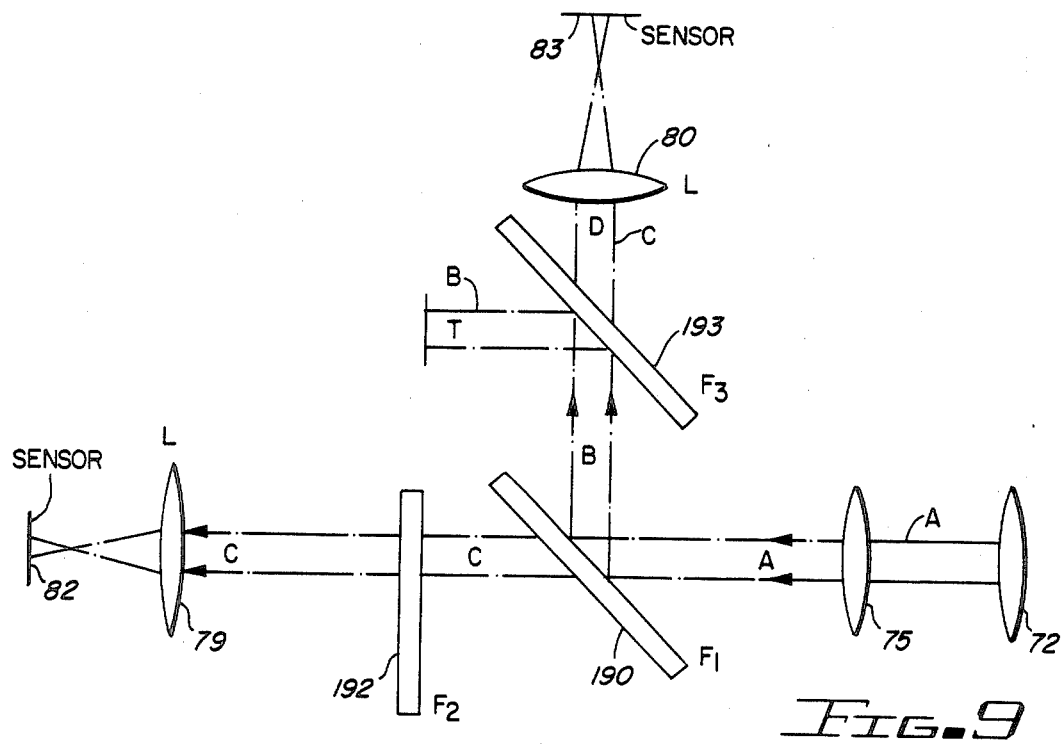
FIG. 9 is a diagrammatic representation of the optical paths within the instrument of FIG. 1.

Referring now to FIG. 8, there is seen driver 175, including elongate shank 177, terminating with a working end 178 and handle end 179. T-handle 180 is carried proximate handle end 170. Bearing surface 182, adjacent working end 178, is sized to be matingly and rotatingly received within bore 173. Perpendicular to cylindrical bearing surface 182 and residing at end 178, is flat bearing surface 183 which may be receivable against edge 149 of the respective filter holder 144 or 147. Cylindrical pin 184 projects from bearing surface 183 along an axis spaced from and parallel to the axis of rotation of cylindrical bearing surface 182. Pin 184 is receivable within slot 174 when bearing surface 182 is received within bore 173.

With filter tray assembly 130 positioned within compartment 158, aperture 155 of filter holder 144 resides proximate the intersection of the axes represented by the broken lines A and C. Similarly, the aperture 155 of filter holder 147 resides proximate the intersection of the axes represented by the broken lines B and C. The elements described with specific reference to FIGS. 7 and 8 provide adjusting means for rotating the filter holders about an axis of rotation to selective angular positions relative the above mentioned axes. Bolt 172, and optionally screw 167, function as locking means for selectively retaining the respective filter holder at a selected one of the positions.

Slot 174, as will be appreciated by those skilled in the art, is defined by a continuous side wall. Contained within the side wall is a pair of spaced parallel subsurfaces which serve as camming surfaces. Pin 184 functions as a cam to bear against a selected one of the camming surfaces. In response to rotation of driver 175, with bearing surface 180 matingly received within bore 173, the eccentric pin 184 bears against the side wall of slot 174 to angularly direct the selected filter holder about the respective axis of rotation. Subsequently, bolt 172 is tightened in the usual manner to immovably fix the filter holder at the selected position.

With further reference to FIG. 8, there is seen means for facilitating alignment and adjustment of filter holder 144 and 147 when filter tray assembly 130 is located within compartment 158. A pair of threaded apertures 185 extend through base plate 24. Each aperture 185 is of a predetermined size and location to expose the immediately previously described adjusting and locking means. To maintain the light tight integrity of case 20, when adjustment of the lens holders 144 and 147 is not desired, each threaded aperture 185 is provided with a mating threadedly engagable cap 187.

First, second, and third filters are held by the filter holders 144, 145 and 147, respectively. In each assembly the filter is held in the respective aperture 155 by a cementious material or other means known to those skilled in the art.

Consistent with an objective function of the instant invention, first filter 190 is chosen to be of a type having a light intensity transmission of approximately fifty percent and centered upon a selected Fraunhofer Line with a bandwidth typically in the range of 10–100 Angstroms at forty-five degrees angle of incidence. Third filter 193 is of a generally similar type, but having a center frequency situated appropriately offset from the selected Fraunhofer Line (i.e., in the continuum) typically in the range 10–100 Angstroms.

Second filter 192 is chosen to have a minimum transmission of approximately forty percent and centered on the selected Fraunhofer Line with a four Angstrom bandwidth at five degrees incidence. The material of fabrication should yield a maximum shift of approximately ten Angstroms over a five degree centigrade change in temperature. A representative material is magnesium fluoride.

For each of the foregoing filters, the given data will be sufficient for the production of the desired filter by one skilled in the art of lens and filter making.

The first filter 190 and third filter 193 are angularly adjustable and lockable at the selected angular position relative the axis of the respective light ray. Second filter 192 is tunable by the operator during use for selective angular adjustment relative the optical path of the light ray extending along the axis A.

As seen in FIGS. 5 and 6, filter holder 145 is angularly pivotal about the axis of pin 164 in a rearward first direction as designated by the arrowed line K and in a reciprocal forward second direction represented by the arrowed line L. Pin 200, projecting upwardly from base plate 132, limits the angular disposition of filter holder 145 in the direction indicated by the arrowed line K. Spring holder 202 is secured to top surface 138 of base 132 at a location spaced from pin 200 in a direction generally indicated by the arrowed line L. Compression spring 203, projecting from holder 202, bears against holder 145 normally biasing same in the direction of arrowed line K against stop 200.

Tuning means for selective angular adjustment of second filter 192 is best described with reference to FIGS. 1 and 2. Adjustment means 204, projecting rearwardly from case 20, is carried proximate the right edge 37 of real panel 33. Rod 205, extending along an axis substantially parallel to the axis represented by the broken line A, extends through aperture 207 in second panel 62 and terminates with end 208, which contactingly abuts filter holder 145 proximate edge 152.

Adjusting means 204 may be readily fabricated from a conventional micrometer head, having barrel 209 and rotatably mounted thimble 210. Barrel 209 is stationarily affixed to panel 33. Thimble 210 is alternatively movable in directions indicated by the arrowed line M and N. In accordance with conventional practice, rotation of thimble 210, in a clockwise direction, results in advancement in the direction of arrowed line M, while counter-rotation yields retraction in the direction of arrowed line N. Calibration indicia 212, cooperating between barrel 209 and 210, micrometrically indicates the relative movement.

Rod 205 is an extensible element moving in extending and retracting directions in response to rotation of thimble 210. Spring 203 reinforces and maintains contact between filter holder 145 and the free end 208 of rod 205. In response to extension of rod 205 in the direction indicated by the arrowed line M, spring 203 is tensioned. In response to retraction of rod 205, in the direction of arrowed line N, spring 203 is relaxed.

In accordance with the foregoing description, it is apparent that a plurality of filter tray assemblies 130 can be made to be interchangeably and replaceably positioned within compartment 58. The tuning means described above insures that each filter 192 can be angularly adjusted to a previously calibrated position. A prior recording of a read-out of the calibration indicia 212 will provide a ready reference for repositioning any given filter.

Optical filter 72 blocks all light having a wavelength lesser than that of visible light. Similarly, optical filter 75 blocks all light having a wavelength greater than that of visible light.

Those skilled in the electronic arts will understand that it is a straightforward matter to simply employ a meter to measure the respective voltage outputs from the photovoltaic sensors 82, 83 to obtain the readings from which the calculations for determining luminescence of the target may be carried out as set forth in previously mentioned U.S. Pat. No. 3,598,994 and the literature covering the U.S.G.S. Fraunhofer Line Discriminator. However, it is desirable to somewhat automate the measuring process to assist the operator and increase the efficiency of operation.

It has thus been found that the field operation of the instrument can be substantially facilitated by employing a simple microcomputer, such as the Octagon SYS-1 (not shown), in conjunction with a commercially available low level amplifier such as the Burr-Brown PGA 100B and a commercially available analog-to-digital converter module such as the Intersil 1CL7109. The Octagon SYS-1 uses a National 8073 microprocessor which features on-board TINY BASIC, a very straightforward language for performing the necessary data manipulations and calculations which result in the direct readout of the signals sensed by the photovoltaic sensors 82, 83 on a digital display 300 which may be, for example, a type PCIM200 manufactured by Printed Circuits International.

Power for the electronics (which, while not shown in detail, are represented in FIG. 2 by the printed circuit board 220 plugged into socket 221) is preferably obtained from a separately housed rechargeable battery pack (not shown) providing twelve volts to the onboard power supply 222 which simply regulates the raw voltage to the close tolerance five volts standard required by the digital electronics and, if different, to regulated split or single-ended supply voltages appropriate to the selected analog electronic circuits.

Selecting the information to be displayed on the readout 300 may be readily accomplished by a knob 302 coupled to a switch (not shown) which selectively connects the terminals of the light sensitive sensors 82, 83 (and other sensors, such as temperature, which might be desired) to the analog-to-digital converter module.

The electronics package, while entirely optional, significantly increases the efficiency and flexibility of the instrument and is preferably incorporated into the instrument.

CALIBRATION AND OPERATION

Those skilled in the art will appreciate that, once the instrument with its inherent features is realized, the methods for effecting calibration and for using the instrument in the field are diverse and subject, to some extent, to personal opinion of the calibrator/operator. A fundamental preliminary calibration step, of course, is to adjust the beamsplitter 190 using its attendant adjustment means to precisely direct the light following the optical path to the sensor 83. Similarly, the third filter 193 may be fine tuned (using its attendant adjustment means) to situate its passband in the continuum in the desired spectral position near the Fraunhofer Line.

It has been found that an individual instrument incorporating a selected individual filter tray assembly constitutes a unique assemblage which must be individually calibrated, particularly as to the second filter 192. Preferably, the calibration instrumentation includes calibration plates of known reflectivity and known zero luminescence and which are employed in conjunction with a light source of scannable spectral characteristics (such as is available from the excitation monochronometer of a Farrand or other make of photospectrometer). In addition, the indicia of the adjustment means 204 (which serves to selectively angularly adjust the second filter 192) should be recorded for at least two different temperatures for which light emitted at the Fraunhofer Line is precisely centered in the passband of the second filter. Within the angular range of adjustment contemplated for the second filter 192, the frequency shift associated with changing the angle of the filter with respect to the light path therethrough is nearly linear. Therefore, it will be appreciated that temperature correction charts and/or curves may be generated for subsequent field use such that the temperature of the second filter 192 can be determined and the result used to manually set the adjustment means 204 to bring the second filter into precise tune for any temperature encountered in the field.

Normalization constants, to account for the transmission differences between the optical "channels" to the sensors 82, 83 in the instrument (as well as slight gain differences in the electronic components which are not common to the two channels) can be obtained by operating the instrument using calibration plates (e.g., certified barium sulfate discs) of known reflectivity and zero luminescence as test targets. With the R and L values known, and the A, B, C, and D readings having been taken, the normalization constants are readily obtained by conventional simultaneous equation solutions. It has been found that these constants may vary with reflectivity such that they may usefully be obtained for several (three or four) reflectivities, typically in the range 0.2–0.9.

The broad purpose of conducting field operations is to obtain reliable A, B, C and D measurements for an unknown target within the field of view. The target may be as simple as a rock, a plant, or virtually any other object for which information as to whether it luminesces under stimulation by sunlight is meaningful. While field technique, like calibration, is subject to individual approach, basic procedural requirements must be followed to insure the integrity of the measurements taken. The following procedure has been found to be sound.

During field operation, frequent temperature readings of the instrument interior in the region of the second filter 192 should be taken and its attendant adjustment means set accordingly to insure that the second filter is tuned with the Fraunhofer Line precisely in the center of its passband. With the target window capped off by cap 104 and the diverter mirror shifted to its alternate position, the diffusing window 102 is aimed directly at the sun and uncorrected A and B readings are taken and recorded. The diffusing window is then capped off, and "dark" readings are taken in the two channels to obtain and record offset correction constants to be subtracted from the A, B, C and D readings. Then, the target window is uncapped, and readings are taken and recorded of two or more calibration plates of known reflectivity and known zero luminescence to provide relative signal strength information under the then current sun illumination conditions. Finally, the C and D readings are taken and recorded for the unknown target. These readings can be subsequently referenced to those contemporaneously taken for the zero luminescence calibration plates, and the difference is regarded as luminescence.

Experience has shown that several unknown targets can be "shot" during a period on the order of a half hour on a clear day before the whole field calibration procedure must be repeated; provided, however, that frequent retuning of the second filter 192 must be performed as the instrument temperature changes. During days in which significant short term changes are experienced in the sun conditions (as when light clouds are passing over), it is necessary to recalibrate more often. Again, experience has shown that best results are achieved on a sunny day with no or few clouds such that conducting field operations on other days may yield unreliable and misleading results.

Figure 10:
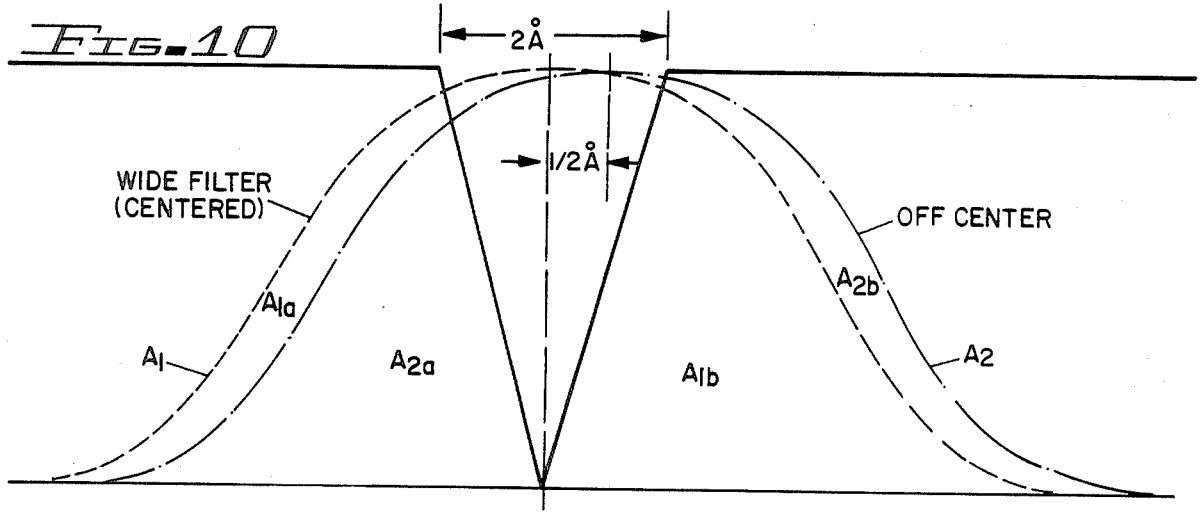
FIG. 10 is a graphic representation of sunlight intensity, chosen in a selected band to include a Fraunhofer Line, and having a corresponding band as viewed by the instrument of the instant invention superimposed thereon.
Figure 11:
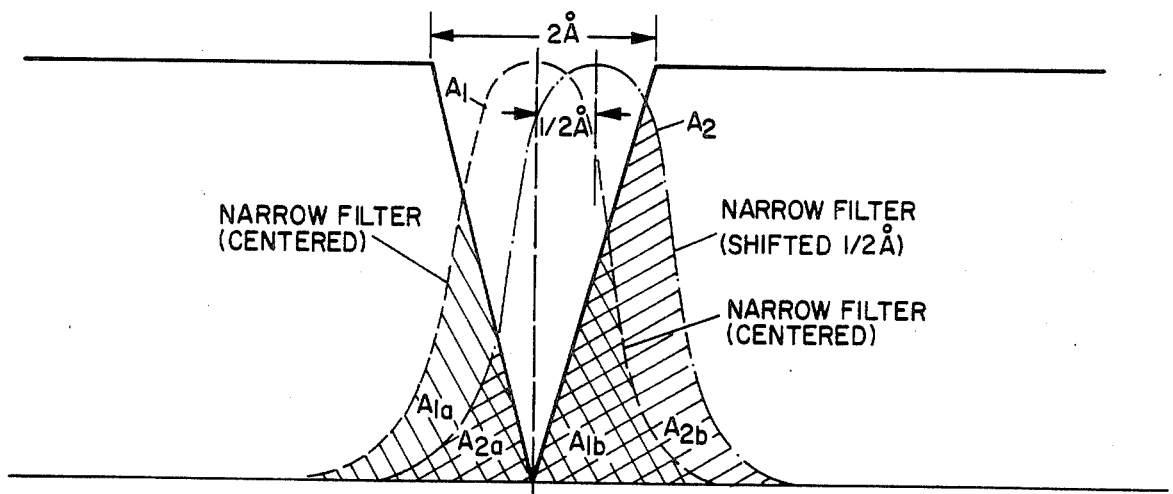
FIG. 11 is an illustration, generally corresponding to the illustration of FIG. 10, except having a prior art view of luminescence light superimposed thereon.

FIGS. 10 and 11 compare a time-shifted resultant obtained with a filtering lens according to the instant invention with the Fabry-Perot type filter of the prior art. Shown in FIG. 10, in solid line, is a graph of sunlight intensity with the corresponding Fraunhofer Line centered at a given wavelength. In comparison to the prior art, the instant invention utilizes relatively wide filters. That is, even though the filters center at a given wavelength, wavelengths within a few Angstroms range still pass through. This results in a wide expansion of wavelengths of the luminescent material being detected. Indicated by broken line $A_1$ in FIG. 10, is the relative increase in intensity at the Fraunhofer Line of reflected light caused by the luminescent radiation of a substance.

Broken line $A_2$ in FIG. 10 shows the filter center frequency shifted 0.5 Angstrom, as may be caused by a variation in temperature. Comparing the intensity levels contained in $A_{1a}$ to that in $A_{2a'}$ and that of $A_{1b}$ to that of $A_{2b'}$ it is immediately apparent that a shift of 0.5 Angstrom due to temperature change will cause a relatively minor variation in the readings.

By way of comparison, FIG. 11 representing the same conditions shows a substantially differing result obtained by the prior art through the use of Fabry-Perot type filters. It is well known that Fabry-Pérot type filters are exceedingly temperature sensitive and that 0.5 Angstrom shift will result from a relatively minor temperature change. As clearly illustrated in FIG. 11, a 0.5 Angstrom shift will provide an inaccurate, unusable readout.

Broken line $A_1$ in FIG. 11 represents a centered reading of luminescent variation of a given substance. Broken line $A_2$ represents a shift reading. By comparing the energy level in $A_{1a}$ to $A_{2a}$ and $A_{1b}$ to $A_{2b'}$ respectively, it is seen that the change in energy reading, under practical field use conditions, will be rendered useless.

The above descriptions are given by way of example only. Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described and disclosed the present invention in such clear and concise terms as to enable those skilled in the art to understand and practice the same, the invention claimed is:

1. An apparatus for receiving a composite ray of light from a target, which composite ray of light includes reflected light having at least one Fraunhofer Line and may include solar induced luminescent radiation and for sensing and measuring the relative value of the luminescent radiation if present, said apparatus comprising:
   a. a body;
   b. a target window carried by said body for receiving said composite ray of light therethrough along a first optical path;
   c. a first optical filter aligned along said first optical path for:
      i. transmitting therethrough a first fraction of said composite ray of light along said first optical path, said first fraction of said composite ray of light being limited to a first selected waveband containing a selected Fraunhofer Line, and
      ii. redirecting the remainder of said composite ray of light along a second optical path;
   d. a second optical filter aligned along said first optical path for limiting the light energy content of light passing therethrough to a second selected waveband which is narrower than said first selected waveband and including, but wider than, said selected Fraunhofer Line;
   e. tuning means for effecting selective angular adjustment of said second optical filter relative said first optical path;
   f. first sensor means aligned along said first optical path for receiving light in said second selected waveband and for sensing the electro-magnetic energy level contained therein;
   g. a third optical filter aligned along said second optical path for transmitting a narrowed waveband in the continuum offset from said selected Fraunhofer Line by a selected frequency difference;
   h. second sensor means aligned along said second optical path for receiving said light in said narrowed waveband in the continuum and for sensing the electromagnetic energy level contained therein; and
   i. indicator means for providing a sensible readout of the energy level sensed by said first and said second sensor means.

2. The apparatus of claim 1 further including a first focusing lens aligned along said first optical path intermediate said second optical filter and said first sensor means for concentrating the electro-magnetic energy contained within said second selected waveband for receipt by said first sensor means.

3. The apparatus of claim 2 further including a second focusing lens aligned along said second optical path intermediate said third optical filter and said second sensor means for concentrating the electromagnetic energy contained within said narrowed waveband in the continuum for receipt by said second sensor means.

4. The apparatus of claim 1 further including means for angularly adjusting said first optical filter relative said first optical path.

5. The apparatus of claim 4 further including means for angularly adjusting said third optical filter relative said second optical path.

6. The apparatus of claim 1 further including viewing scope means carried by said body, said viewing scope means having an ocular lens disposed in a position for receiving at least a portion of the composite ray of light received through said target window.

7. The apparatus of claim 1 further including a fourth optical filter aligned along said first optical path intermediate said target and said first optical filter for blocking from said first optical filter a selected waveband of said composite ray of light having a wavelength shorter than the wavelength of visible light.

8. The apparatus of claim 7 further including a fifth optical filter aligned along said first optical path intermediate said target and said first optical filter for blocking from said first optical filter a selected waveband of said composite ray of light having a wavelength longer than the wavelength of visible light.

9. The apparatus of claim 1 further including viewing scope means carried by said body for receiving light redirected from said second optical path by said third optical filter.

10. The apparatus of claim 1 further including:
    a. a direct light receiving lens carried by said body for receiving a ray of direct light therethrough along a third optical path; and
    b. diverter means for selectively redirecting said ray of direct light from said third optical path along said first optical path in a direction toward said first sensor means.

11. The apparatus of claim 10 wherein said diverter means redirects said ray of direct light onto said first optical path at a location intermediate said target window and said first optical filter.

12. The apparatus of claim 1 in which the bandwidth of said first optical filter falls within the range 10–100 Angstroms.

13. The apparatus of claim 12 in which the bandwidth of said third optical component filter falls within the range 10–100 Angstroms.

14. An apparatus particularly adapted as a portable, handheld instrument for receiving a composite ray of light from a target for sensing and measuring the relative value of luminescent radiation present in said composite ray of light and which composite ray of light includes reflected light having at least one Fraunhofer Line, said apparatus comprising:
    a body including means forming a target window for receiving said composite ray of light therethrough along a first straight line optical path;
    a first optical filter aligned along said first optical path for transmitting therethrough a first fraction of said composite ray of light along said first optical path and of a first selected waveband containing a selected Fraunhofer Line, and redirecting the remainder of said composite ray of light along a second optical path extending at an angle to said first optical path;
    a second optical filter aligned along said first optical path for limiting the light energy content of light passing therethrough to a second selected waveband including, but wider than, said selected Fraunhofer Line;
    first sensor means aligned along said first optical path for receiving light in said second selected wave band and for sensing the electro-magnetic energy level contained therein;
    a third optical filter aligned along said second optical path for transmitting a narrowed waveband in the continuum offset from said selected Fraunhofer Line by a selected frequency difference;

second sensor means aligned along said second optical path for receiving said light in said narrowed waveband for sensing the electro-magnetic energy level contained therein; and viewing scope means carried by said body having an ocular lens disposed along a third optical path for receiving at least a portion of said composite ray of light which is redirected by said first optical filter and said third optical filter for directly viewing an image through said target window.

15. The apparatus set forth in claim 14 including:

support means disposed on said body for supporting said first, second and third optical filters for movement relative to said support means, said support means being mounted on said body for removal therefrom.

* * * * *